United States Patent [19]

Duong-Van et al.

[11] Patent Number: 5,439,004
[45] Date of Patent: Aug. 8, 1995

[54] DEVICE AND METHOD FOR CHAOS BASED CARDIAC FIBRILLATION DETECTION

[75] Inventors: Minh Duong-Van, Mountain View; Mark J. Meltzer, San Francisco, both of Calif.

[73] Assignee: Ventritex, Inc., Sunnyvale, Calif.

[21] Appl. No.: 173,797

[22] Filed: Dec. 23, 1993

[51] Int. Cl.⁶ .............................. A61B 5/046
[52] U.S. Cl. ........................................ 128/705
[58] Field of Search ........................ 128/702, 705

[56] References Cited

U.S. PATENT DOCUMENTS 4,202,340  5/1980  Langer et al. ............... 128/702
4,732,157  3/1988  Kaplan et al. ............... 128/702
5,201,321  4/1993  Fulton ........................ 128/702

Primary Examiner—William E. Kamm
Attorney, Agent, or Firm—Steven M. Mitchell; Mark J. Meltzer

[57] ABSTRACT

A system and method for detecting ventricular fibrillation based on chaos theory. A Poincaré plot of the amplitude of the ECG signal is generated and used to detect the presence of fibrillation. The plot is monitored for the data points drifting off the plot axes. Upon detecting such drift, the presence of ventricular fibrillation is confirmed. The system and method may be used as a primary detection scheme or as a backup system to reconfirm fibrillation detection using conventional techniques.

9 Claims, 5 Drawing Sheets

DEVICE AND METHOD FOR CHAOS BASED CARDIAC FIBRILLATION DETECTION

FIELD OF THE INVENTION

The present invention relates to cardiac arrhythmia detection and control devices, and more specifically to a system which provides ventricular fibrillation detection based on chaos theory.

BACKGROUND OF THE INVENTION

The human heart is divided into four chambers, two upper chambers called atria and two lower chambers called ventricles. The heart's function is to pump blood through the body's circulatory system. A healthy heart at rest typically beats between 60 and 100 times per minute and will pump over 1,800 gallons of blood per day. Each normal heart beat is the result of electrical signals generated at a precise area in the right atrium, called the sino-atrial node, the heart's natural pacemaker. These electrical signals cause a physical contraction of the atria, which pump blood into the ventricles. The electrical impulses then continue to the ventricles, causing them to contract and distribute blood throughout the body.

Arrhythmias, abnormal rhythms of the heart muscle, arise from numerous causes, including tissue damage due to previous heart attacks, congenital defects and certain diseases. Arrhythmias can originate in either the atria where they are generally not life-threatening, or the ventricles, where they can significantly interfere with the pumping of oxygenated blood and can therefore be life-threatening. During an arrhythmia, the heart beats either too slowly or too rapidly. An abnormally slow heart rate, generally defined as a heart rate below 50 beats per minute, is known as bradycardia. This condition is usually treated by implanting a bradycardia pacemaker, a device that monitors the heart and delivers electrical impulses when necessary to increase the heart rate. A more serious arrhythmia occurs when the ventricles beat at an abnormally rapid rate, a condition known as ventricular tachycardia. In ventricular tachycardia, abnormal electrical signals occur in the ventricles. When the ventricles beat at an abnormally rapid rate, they do not have sufficient time to fill with blood prior to each contraction and therefore less blood is pumped out of the heart. As a result, less oxygen is carried to the tissues and organs of the body. This lack of oxygen can cause dizziness, unconsciousness, cardiac arrest and, ultimately, death.

Episodes of ventricular tachycardia occur unpredictably and tend to become more serious over time. Ventricular tachycardia can progress to the most serious type of cardiac arrhythmia, ventricular fibrillation. In ventricular fibrillation, the heart's normal electrical impulses become disorganized and erratic. Unlike ventricular tachycardia, during which the heart continues to contract in an organized fashion, in ventricular fibrillation the heart quivers and ceases to pump blood. As a result, the individual's blood pressure falls to nearly zero. If ventricular fibrillation is not terminated quickly, the individual will experience a sudden cardiac death (SCD) episode during which the individual will become unconscious as a result of the heart's failure to pump oxygenated blood to the body's tissues and organs, and without prompt medical intervention, typically will die.

A well-known device for treating patients with arrhythmias is an implantable cardioverter/defibrillator (ICD) which is an electronic device that is implanted in the patient and is designed to monitor the patient's heartbeat and deliver electric pulses or shocks to the heart to terminate arrhythmias. A typical ICD system consists of a device for pulse generation, defibrillation leads and pacing/sensing leads. The pulse generator contains the battery and electronic circuitry that monitors the patient's heartbeat and delivers therapy upon detection of a ventricular tachyarrhythmia. The pacing/sensing leads are insulated wires that connect the pulse generator to the heart and allow the device to sense the patient's heartbeat. These leads also carry electrical pulses for pacing. The defibrillation leads carry electrical shocks to terminate ventricular tachycardia and ventricular fibrillation. The defibrillator is surgically implanted beneath the skin in the patient's abdomen and the defibrillation leads are typically either epicardial patch electrodes connected to the exterior of the heart or endocardial leads inserted transvenously into the chambers of the heart. An endocardial lead system may also include a subcutaneous patch electrode. An ICD system of this type is described in U.S. Pat. No. 5,014,701 to Pless et al., which is assigned to the assignee of the present application and which is incorporated herein by reference.

An important feature of an ICD is the arrhythmia detection system. One of the earliest techniques for detection is described in U.S. Pat. No. Re 27,757 to Mirowski in which a pressure transducer is positioned in the right ventricle of a patient's heart. When the sensed pressure falls below a preset threshold, the device determines the presence of an arrhythmia and a therapy is delivered. More recent ICD systems rely primarily on an evaluation of the sequence of cardiac event timing intervals from a sensed electrogram (ECG). Various algorithms are applied to the detected timing intervals to determine the presence of an arrhythmia. Ventricular fibrillation is typically detected based strictly on heart rate (or interbeat interval) while tachycardia is detected based on rate along with other parameters such as sudden onset, stability, sensed physiological activity (exercise) and ECG waveform morphology. Certain rate boundaries are programmed into the ICD for each patient and these boundaries set up specific detection zones. These systems are not entirely satisfactory because there is still difficulty in making certain determinations, such as for example distinguishing between ventricular fibrillation and atrial fibrillation. An inappropriate defibrillation shock is very painful to the patient and may actually induce fibrillation. It would therefore be desirable to have another detection system which could be used independently or in conjunction with prior art detection systems for detecting ventricular fibrillation.

Researchers have found that the electrical activity of the heart reflects the activity of a dynamical system. A dynamical system is a system which is time dependent and may be described with differential equations having at least three independent dynamical (time dependent) variables. The equations must contain a nonlinear term which couples several of the variables. This coupling is a manifestation of what can be considered as feedback. The theory used to describe such systems is known as chaos theory and systems which exhibit this type of behavior are called dynamical or chaotic systems. Dynamical systems such as the heart can exhibit both periodic and chaotic behavior depending on certain system parameters. These parameters appear as constants in the differential equations describing the system. The chaotic behavior exhibited by the heart is not immediately obvious when looking at an ECG. One way which investigators have used for observing the chaotic behavior of the heart has been to plot the interbeat spacing at a time n against the interbeat spacing at time n+1. Such a plot is known as a Poincaré map or return map. Using chaos theory as a tool to characterize tachyarrhythmias and as a basis for arrhythmia control would thus be beneficial.

A system which uses chaos theory to diagnose vulnerability of patients to cardiac arrhythmias is disclosed in U.S. Pat. No. 5,201,321 to Fulton. An analysis is applied to R—R interval measurements to generate a specific indication of vulnerability to lethal myocardial infarction. This technique is not, however, used for the characterization of fibrillation as is needed in an ICD.

It is an object of the invention to provide an improved system and method for detecting ventricular fibrillation.

It is a further object of the present invention to utilize the dynamical nature of the heart as exhibited in ECG signals to detect fibrillation.

SUMMARY OF THE INVENTION

The present invention provides a system and method based chaos theory for detecting ventricular fibrillation. A return map is generated based on the amplitude of the sensed ECG signal and this is used to determine the presence of a ventricular fibrillation. The points of the plot are very tightly contained along the axes of the return map in the absence of fibrillation. When the fibrillation episode starts, the return map points rapidly drift off the axes. This is detected and may be used as a primary detection of fibrillation or as a backup confirmation of the presence of fibrillation. The system may also be used to distinguish ventricular fibrillation from other tachyarrhythmias.

In practicing a preferred embodiment of the invention, a patient's ECG signal is obtained using a sensing lead placed within the right ventricle of the heart. This signal is amplified and digitized using an analog-to-digital converter. The signal is sampled at approximately 2 millisecond intervals and the amplitude is temporarily stored in memory. The amplitude of each data point is plotted against the amplitude of the ECG signal 88 milliseconds (44 data points) later. A deadband around the plot axes is created and points on the plot falling outside the deadband are indicative of fibrillation.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
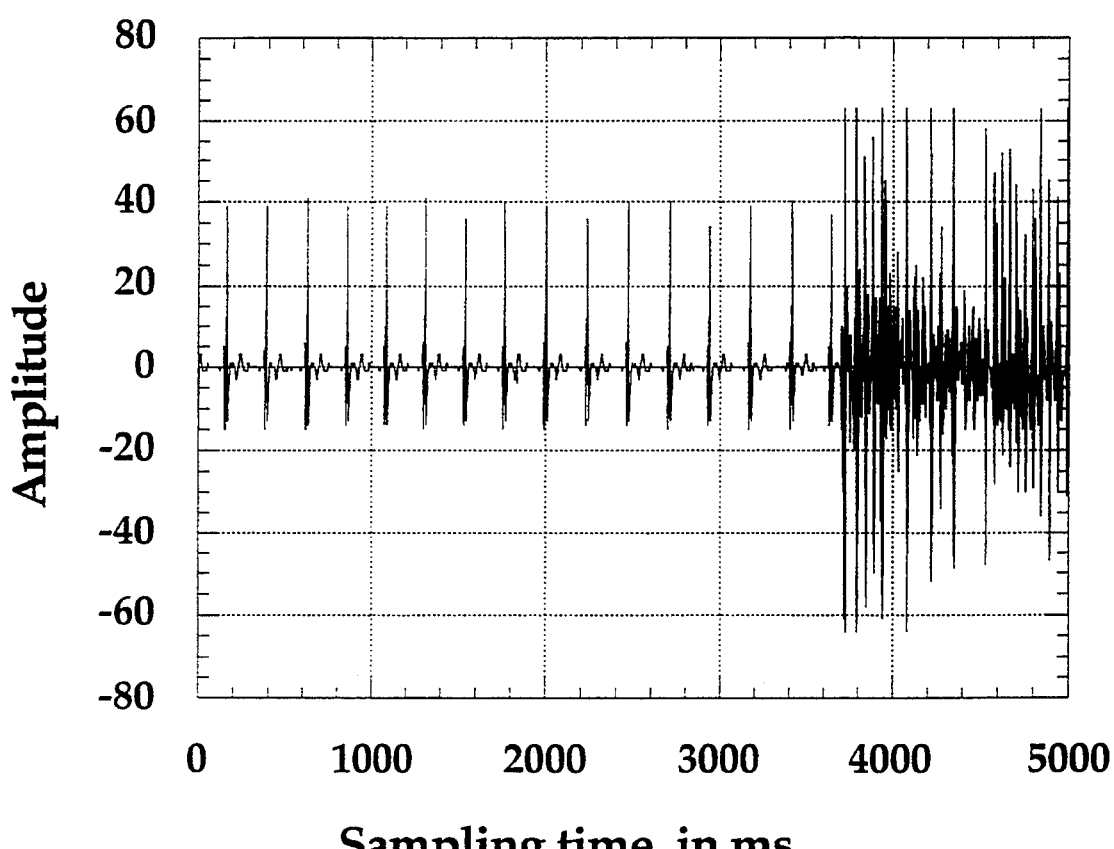
FIG. 1 shows an ECG plot as it transitions from normal sinus rhythm to fibrillation.
Figure 2A:
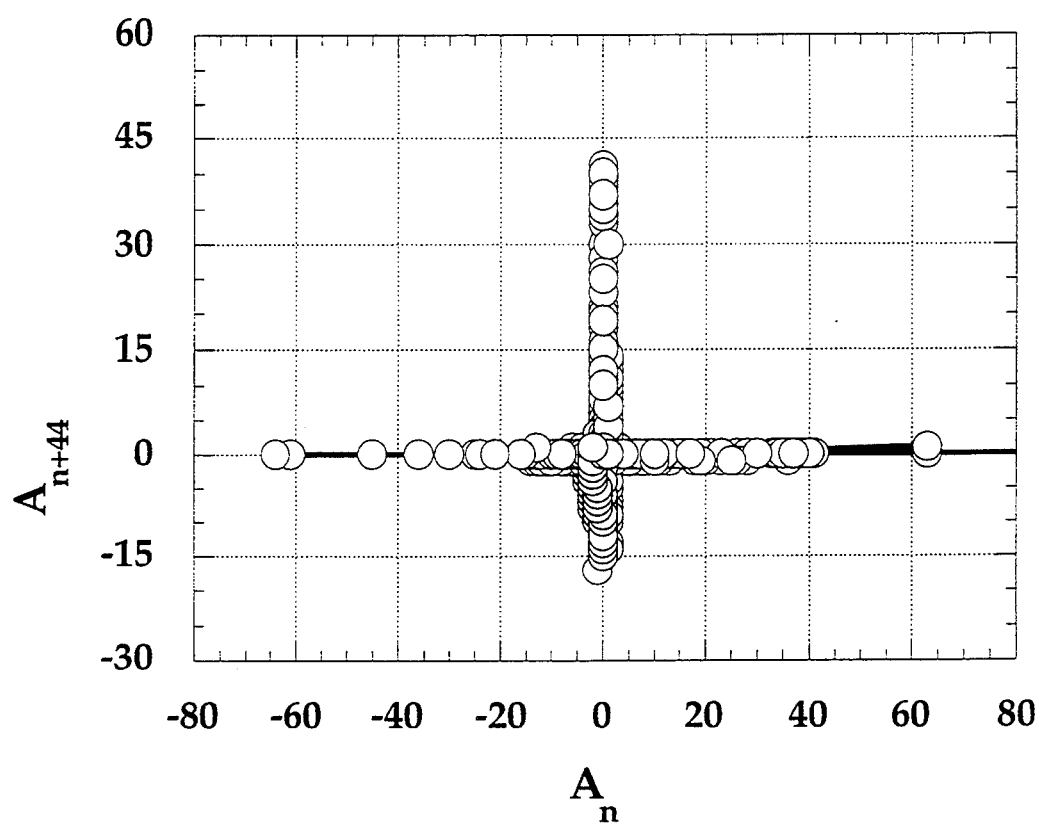
FIG. 2A shows a plot of the Poincaré map of ECG amplitude for the sinus rhythm portion of the ECG of FIG. 1.
Figure 2B:
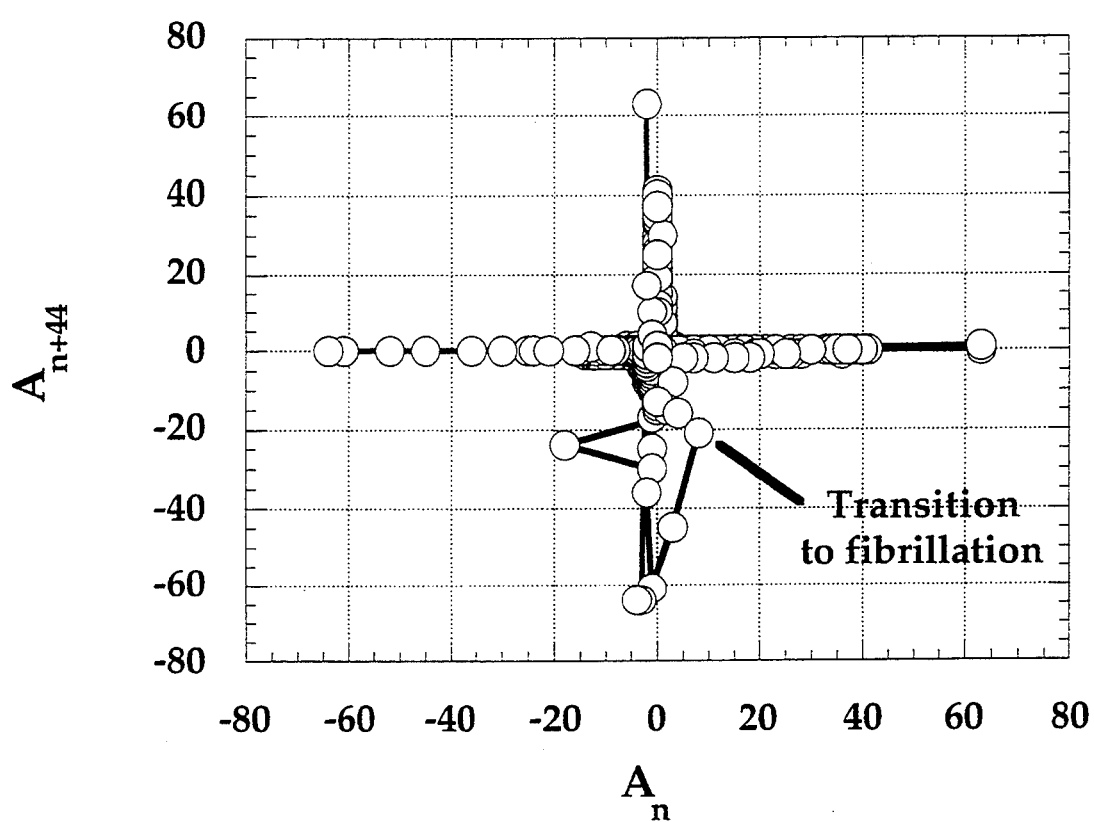
FIG. 2B shows a plot of the Poincaré map of ECG amplitude for the transition to fibrillation of the ECG shown in FIG. 1.
Figure 2C:
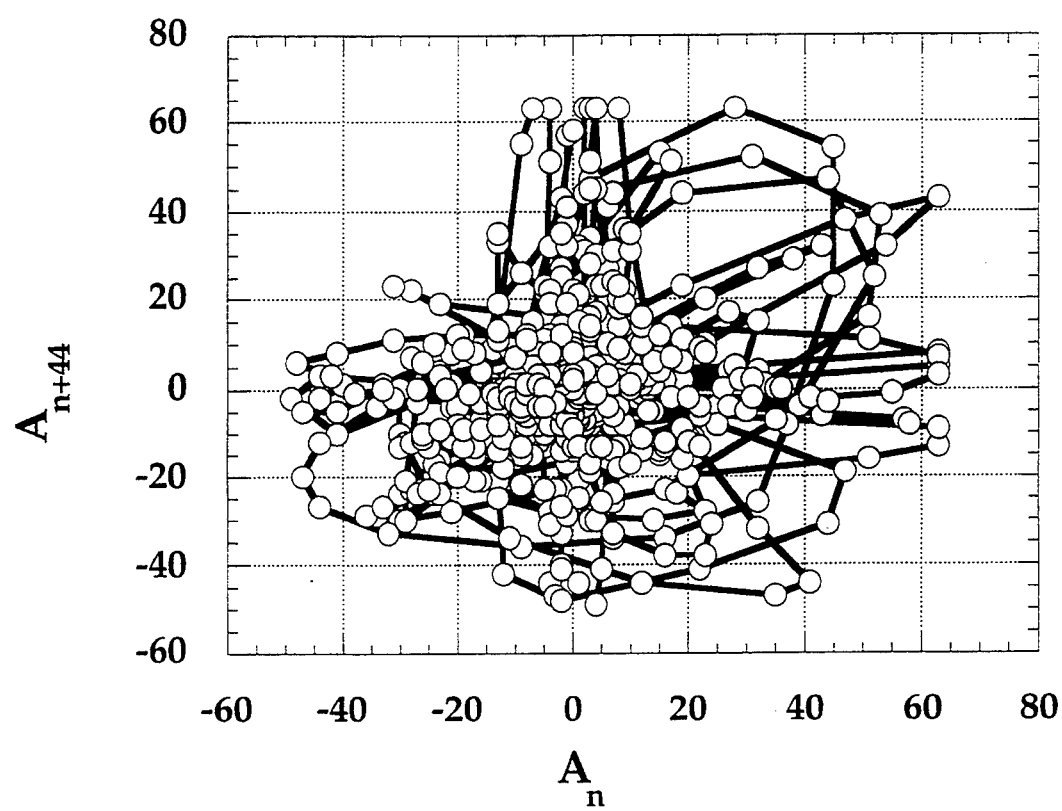
FIG. 2C shows a plot of the Poincaré map of ECG amplitude for the portion of the ECG shown in FIG. exhibiting fibrillation.

It has been discovered that the amplitude of the electrocardiogram (ECG) from a patient's heart provides an extremely useful representation of the dynamical system of the heart. Referring to the drawings, FIG. 1 shows an ECG plot as it transitions from normal sinus rhythm to fibrillation. FIG. 2A shows a plot of the Poincaré map or return map of ECG amplitude for the sinus rhythm portion of the ECG of FIG. 1. FIG. 2B shows a plot of the Poincaré map of ECG amplitude for the transition to fibrillation of the ECG shown in FIG. 1 and FIG. 2C shows the Poincaré map of the ECG during fibrillation. The ECG plot of FIG. 1 covers about 8 seconds with 4000 data points each taken at 2 milliseconds apart. For the particular ECG of this example, the delay time for the return map, as plotted in FIGS. 2A–2C, has been found to be 0.088 seconds or 44 data points. The ECGs of different patients may exhibit different characteristic delay times which can be determined at the time of implanting an ICD or during later testing when the ICD may be reprogrammed. FIGS. 2A–2C show the amplitude of the ECG at time n plotted against the amplitude at time n+44. The plot of FIG. 2A shows a pattern with a high degree of organization for normal heart rhythm. It can be seen that the data points lie within clearly defined regions of the axes of the plot. This pattern begins to break up as the signal transitions to fibrillation in FIG. 2B. FIG. 2C provides the Poincaré plot for the ECG of FIG. 1 of the heart in fibrillation, clearly exhibiting chaotic behavior. This behavior is used to provide a clear indication for an ICD of the presence of fibrillation in a the patient's heart.

Figure 3:
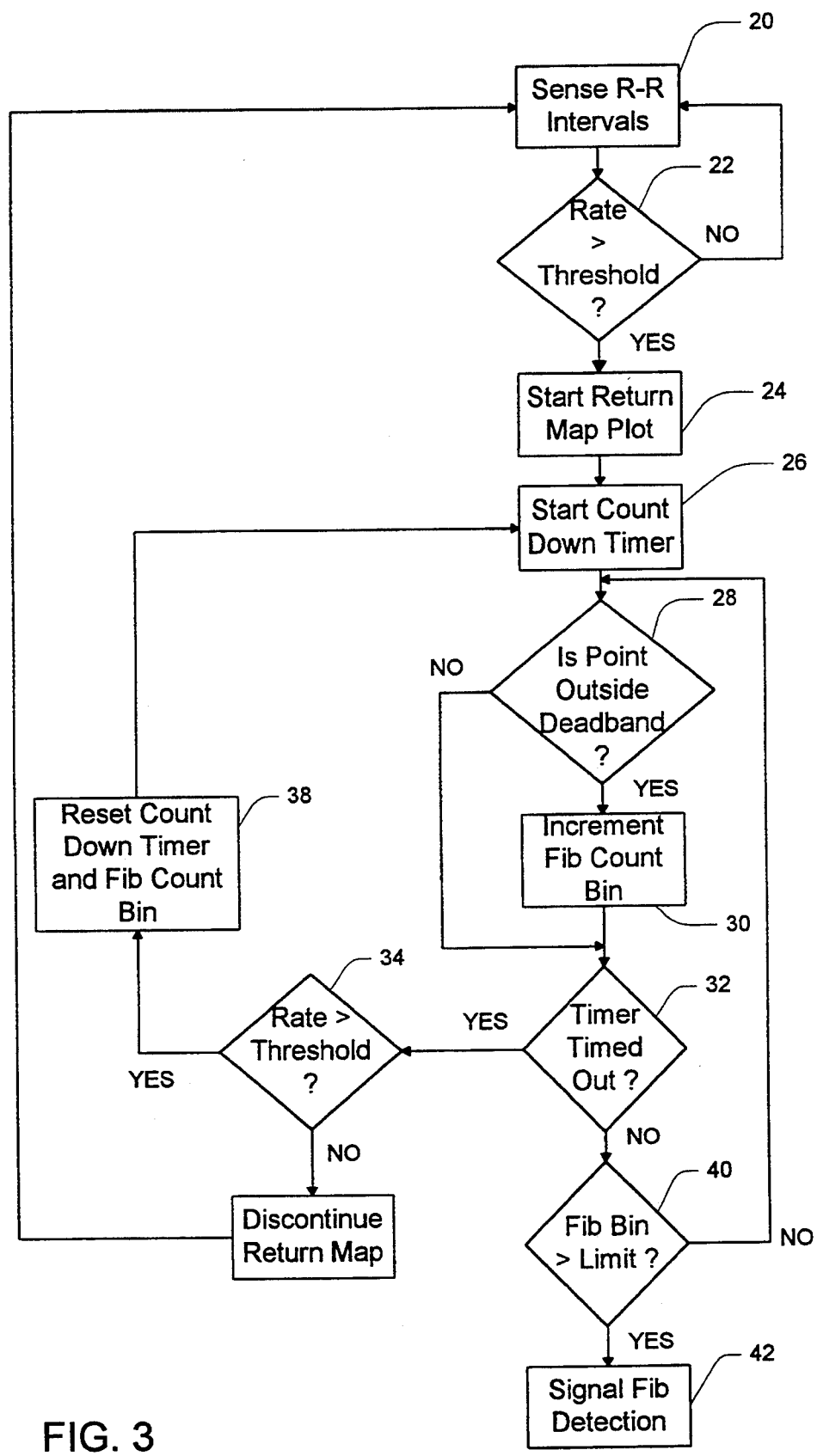
FIG. 3 is a flow chart illustrating the steps of the invention used to detect fibrillation.

Detection of fibrillation using the invention will now be discussed with reference to the flowchart of FIG. 3. The invention may be easily implemented in software in prior art ICDs such as the one described in U.S. Pat. No. 5,014,701 to Pless et al. An ICD with which the invention is used has a sensing lead coupled to the patient's heart, typically in the apex of the right ventricle. This sensing lead provides an analog ECG which is amplified and then digitized with an analog-to-digital converter. The digitized ECG is then used in several ways. Conventional R—R interval sensing is performed as shown in step 20. A determination is then made at step 22 whether the heart rate sensed from the R—R intervals exceeds a preset threshold. This threshold may be the fibrillation threshold for the ICD or may be lower in what is considered the tachycardia range. By overlapping into the tachycardia range, the method of the invention may be used to discriminate between tachycardia and fibrillation near the interface of the two rate ranges. If the rate does not exceed the threshold, the system loops back. Essentially, the system of the invention does not initiate operation until a high rate is detected from R—R interval sensing. While the method of the invention could be continuously running, this is not necessarily a preferred mode since this may consume excess power.

If the heart rate does exceed the threshold, the Poincaré plot is started at block 24. Next, at step 26, a count down timer is started. As discussed above, the plot is defined by the amplitude of each point against a point 0.088 seconds later. Because of this, the count down timer is not started until the system has had time to plot the first point. For each point, the system then determines at decision block 28 whether the point is outside a deadband. This can be easily accomplished by looking at the x,y coordinates of each point. The absolute value of the x coordinate is generated and a determination is made of whether it is greater than a threshold. If it is not, then the point is on or near the y-axis and the point is determined not to be outside the threshold. If the x coordinate is greater than the threshold, then the same step is performed for the y coordinate. If the y coordinate does not exceed the threshold then the point is on or near the x-axis and thus not outside the deadband. Otherwise, if the y coordinate exceeds the threshold, then the point is outside the deadband and is a possible indicator of fibrillation. The system requires a number of such indications within the period of the count down timer so that it does not misdetect noise or random fluctuations in the ECG signal as fibrillation. Clearly, other techniques for this determination are possible, such as using a running ratio of the number of points outside the deadband to the number of points in the deadband. Once the ratio exceeds a preset limit, a fibrillation indication signal is generated.

If a point is outside the deadband in decision block 28, a fib count bin is incremented at block 30. If the point is not outside the deadband, the fib count bin is not incremented. In either case, the status of the count down timer is next checked at decision block 32 to determine if the timer has timed out. If the timer has timed out, this indicates that an insufficient number of outside the deadband points have been detected indicating the absence of fibrillation. In that case, the rate threshold is checked again at block 34. If the rate is not still above the threshold, the return map is discontinued at block 36 and the system returns to the standby rate sensing mode. If, however, the rate threshold is still exceeded, the count down timer and fib count bin are reset at block 38 and the count down timer is started again at block 26.

If the count down timer has not timed out at step 32, the fib bin limit is checked at step 40. The limit is programmable and is set based on experience with the system. A count limit of greater than about 10 for a count down timer having a period of about 1 to 4 seconds will be effective. If the fib bin limit is not exceeded, the system loops back to look at the next point on the return map. In the event the fib count limit is exceeded, a signal indicating-fibrillation is sent to the control microprocessor at step 42.

The generation of a "plot" in connection with this invention is not limited to an actual visually perceptible plot such as may be generated on a CRT screen or by a pen plotter. The word "plot" as used herein includes mathematical equivalents wherein no graphic output is generated and the entire process, including the detection of points lying outside a specified area of said "plot", is done in software.

It should be understood that various alternatives to the embodiments of the invention described herein may be employed in practicing the invention. For example, the system and method of the invention can be used in an external defibrillator. It is thus intended that the following claims define the scope of the invention and that structures and methods within the scope of these claims and their equivalents be covered thereby.

What is claimed is:

1. A method of detecting fibrillation of a patient's heart comprising the steps of:
   (a) sensing a signal from said patient's heart;
   (b) generating a Poincaré plot of the amplitude of said signal;
   (c) identifying a specified area of said plot indicative of the absence of fibrillation; and
   (d) determining the presence of fibrillation by detecting the presence of points in said plot which lie outside said specified area of said plot.

2. The method according to claim 1 wherein said step of sensing includes sensing an ECG signal.

3. The method according to claim 2 wherein said step of identifying includes specifying a deadband around the axes of said plot and said step of determining includes detecting the presence of points outside said deadband.

4. The method according to claim 2 and further including the steps of detecting R—R intervals from said EGG, identifying a heart rate from said detected R—R intervals, comparing said heart rate with a predetermined threshold, and initiating said step of generating a Poincaré plot only if said heart rate based on said R—R intervals is greater than said predetermined threshold.

5. A device for detecting fibrillation of a patient's heart comprising:
   means for sensing an ECG signal from said patient's heart;
   means for generating a Poincaré plot of the amplitude of said ECG signal; and
   means for determining the presence of fibrillation based on the location of points within said Poincaré plot.

6. A device according to claim 5 wherein said means for determining includes means for identifying a specified area of said plot indicative of the absence of fibrillation and means for detecting the presence of points on said plot which lie outside said specified area of said plot.

7. A device according to claim 6 wherein said means for identifying a specified area of said plot includes means for specifying a deadband around the axes of said plot.

8. A method of discriminating between fibrillation and other tachyarrhythmias of a patient's heart comprising the steps of:
   (a) sensing an ECG signal from said patient's heart;
   (b) analyzing said ECG signal to detect the presence of a tachyarrhythmia;
   (c) generating a Poincaré plot of the amplitude of said ECG signal;
   (d) identifying a specified area of said plot indicative of the absence of fibrillation; and
   (e) determining whether a detected tachyarrhythmia is fibrillation by detecting the presence of points in said plot which lie outside said specified area of said plot.

9. The method according to claim 8 wherein said step of identifying a specified area of said plot includes specifying a deadband around the axes of said plot and wherein said step of determining includes detecting the presence of points outside said deadband.

* * * * *